Figure 1:
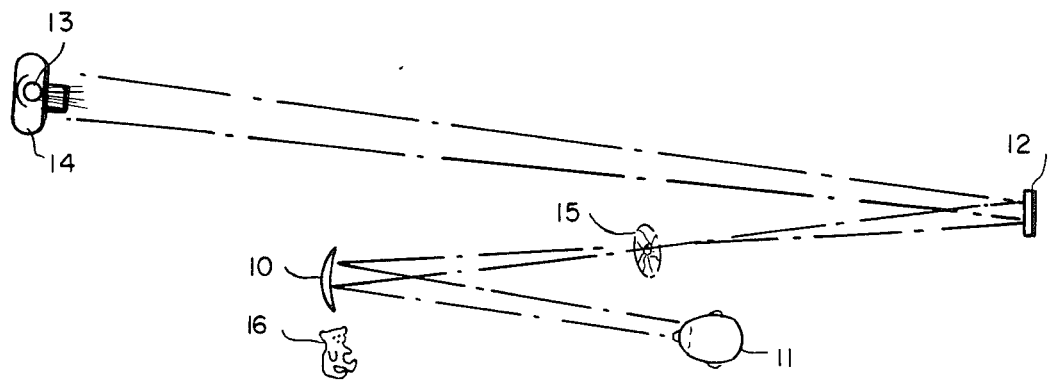

United States Patent [19]

Thorn

[11] Patent Number: 4,755,044
[45] Date of Patent: Jul. 5, 1988

[54] REMOTE OPHTHALMOSCOPE AND FUNDUS PHOTOGRAPHY UNIT

[75] Inventor: Frank Thorn, Newton, Mass.

[73] Assignee: Massachusetts Institute of Technology

[21] Appl. No.: 816,267

[22] Filed: Jan. 6, 1986

[51] Int. Cl.$^4$ ............................................. A61B 3/14
[52] U.S. Cl. ..................................... 351/206; 354/62
[58] Field of Search ............... 351/206, 205, 207, 208; 354/62

[56] References Cited

U.S. PATENT DOCUMENTS

| | | | |
|---|---|---|---|
| 3,217,622 | 11/1965 | Yutak Kiyono | 351/206 |
| 3,927,933 | 12/1975 | Humphrey | 351/237 |
| 4,132,466 | 1/1979 | Matsumura | 351/207 |
| 4,227,780 | 10/1980 | Ohta et al. | 351/208 |

Primary Examiner—Deborah L. Kyle
Assistant Examiner—Michael J. Canore
Attorney, Agent, or Firm—Robert F. O'Connell

[57] ABSTRACT

A system for performing an examination of the eye of a subject which uses a source of light and a concave mirror for focusing such light at a selected region of the fundus of the eye so as to form an enlarged optical image of the selected region at a selected spatial region which is remote from the eye. An ophthalmoscope, or camera, or other viewing instrument is then focused at the selected spatial region to permit the selected region of the eye to be viewed either immediately or photographed for subsequent viewing.

7 Claims, 1 Drawing Sheet

REMOTE OPHTHALMOSCOPE AND FUNDUS PHOTOGRAPHY UNIT

The Government has rights in this invention pursuant to Contract Number NIH-5-R01-EY01191-11 awarded by the National Eye Institute.

INTRODUCTION

This invention relates generally to techniques for ophthalmoscopically examining the fundus of the eye and, more particularly, to an improved technique for permitting such examination to occur without placing any examining objects near the eye and without requiring mydriasis.

BACKGROUND OF THE INVENTION

In current eye examinations, the techniques utilized can be referred to as either direct or indirect ophthalmoscopy. Direct ophthalmoscopy is normally a principal part of every eye examination in which the examiner utilizes a conventional hand-held ophthalmoscope in order to examine the fundus. In accordance with such technique the examiner's eye is normally pressed to the ophthalmoscope device and the instrument is placed as close to the eye as possible, usually less than 1 cm. Such technique permits close and direct examination of the fundus, i.e. a relatively narrow retinal region.

In order to access a wider retinal area, for example, when injury or disease is involved, indirect ophthalmoscopy is used wherein a relatively large lens is held approximately 5 cm. from the eye so as to provide an image of the fundus region at a location in which an appropriate camera can be used to photograph such image. Such cameras, characterized as "fundus cameras," normally require a special design to provide wide angle photography of a curved surface and provide a permanent record of the retinal appearance so as to permit a later more in-depth examination thereof.

In both instances an instrument must be placed relatively close to the patient's face, i.e., within a few centimeters, or less. With some patients, e.g. children, animals, or even wary adults, such technique can be unduly upsetting and can even cause a traumatic experience for the patient. Moreover, in order to photograph or provide some other permanent display of the fundus, it is necessary that the patient's head remain almost absolutely still since any motion, however slight, will tend to distort or destroy the image created. Moreover, in order to achieve the ability to see a wide region of the retina it is necessary to dilate the pupil by utilizing appropriate medication which produces mydriasis. In some instances in order to perform the examination the patient must be sedated or placed under firm restraint, techniques which severely restrict the opportunity for routine fundus examination.

Because of such disadvantages, it is desirable, particularly when examining an unanesthetized or unsedated infant, young child, animal, or a wary patient of any age, to avoid having to place any objects, and particularly medical instrumentation objects, at or near the patient's face. Further, it is desirable to provide an examination technique which permits some minor movement in the position of the eye during the examination procedure without unduly distorting the image achieved. Further it is desirable to devise a technique which permits an image to be formed of a relatively large region of the retinal area without the use of mydriasis so as to permit non-mydriatic fundus photography.

BRIEF SUMMARY OF THE INVENTION

In accordance with the invention a relatively large, relatively low-power, concave mirror is utilized during an eye examination in place of a high power convex lens which is normally used, particularly in indirect ophthalmoscopy. The mirror is used to focus a light source at the pupil of a patient's eye and serves to illuminate the retina. In turn, the eye's optics produce an image of a selected region of the illuminated fundus in space, which image can then be photographed or viewed ophthalmoscopically.

In using the technique of the invention the closest physical element to the eye, i.e., the concave mirror, can be at least 0.5 meter or more away and generally it is found that in most applications of the invention the mirror will be positioned at a distance from the eye which can be greater than one and up to two times the focal length of the mirror. The mirror is designed so that its focal length is about 0.8 of the distance to the pupil of the eye, i.e., the mirror surface is placed at about 1.25 times the focal length from the patient's eye. The image of the pupil of the eye can thereby be focused at a point which is five times the focal length from the mirror and is magnified by four times. A camera can be positioned at this point to look through the pupil image and be focussed so as to photograph the image of the fundus, which is usually one meter from the concave mirror, for subsequent examination. Alternatively an ophthalmoscope can be used instead so that a simple, on the spot, examination can be performed on the fundus image which is produced by the concave mirror through the ophthalmoscope. Whether a camera or an ophthalmoscope is used for examination, in either case no part of the overall apparatus need be placed close enough to the eye to create a disturbing environment for the patient. Accordingly, the upsetting nature of most eye examinations in which an instrument must be held extremely close to the patient's eye is avoided. Moreover, such a system and technique permits some movement of the patient's head and eye without unnecessary distortion of the image which is produced. Because the pupil is magnified at the camera or ophthalmoscope, the need for mydriasis becomes less important and in most cases can be avoided altogether.

DESCRIPTION OF THE INVENTION

The invention can be described in more detail with help of the accompanying drawings.

Figure 2:
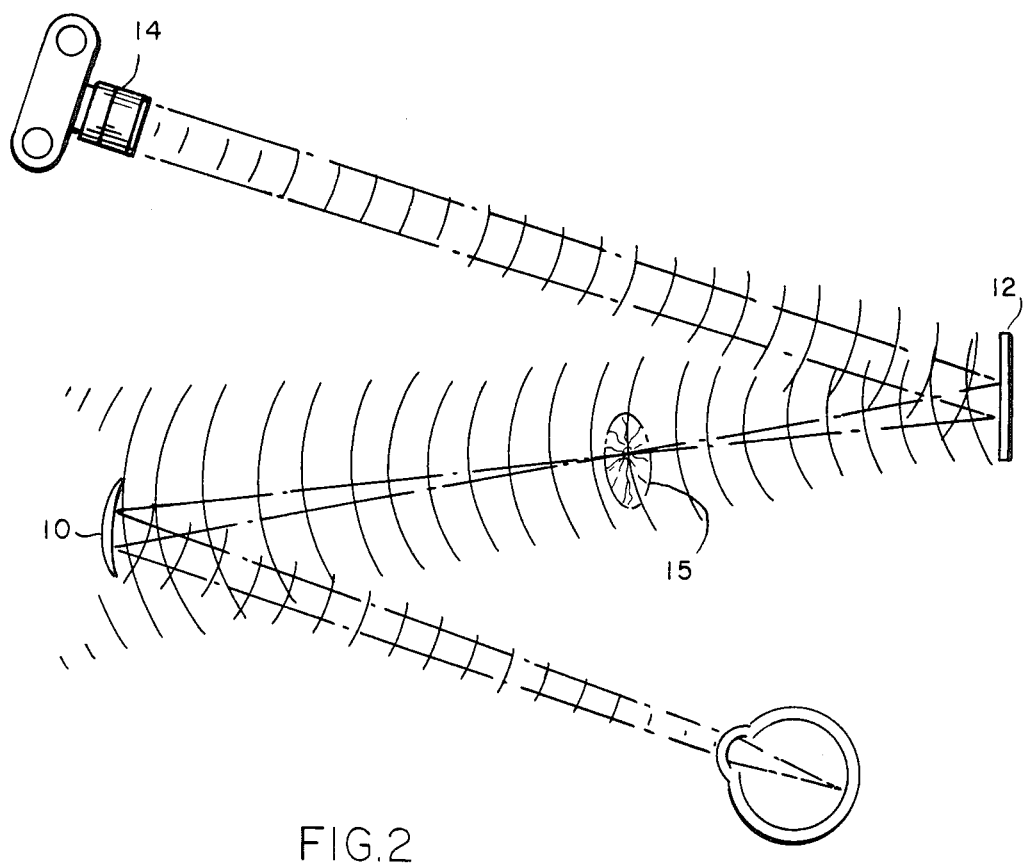

FIG. 1 depicts a diagram of the optical elements used in the invention and their relationship to each other and to the patient; and FIG. 2 depicts a diagram representing the optical paths used for illuminating the fundus and focussing the fundus image.

As can be seen in the particular embodiment of FIG. 1, a relatively large concave mirror 10 is positioned at a location remote from, and at a relatively small angle with reference to, a patient's head 11. For example, the mirror may be an 8-inch, one diopter, concave mirror. One such mirror would be available, for example, from Edmund's Scientific Company of Barrington, N.J. The mirror has a focal length of one meter. A flat mirror 12 is postioned at a location which is two meters from concave mirror 10 and at a relatively small angle with respect thereto to provide a folded optical path between the concave mirror 10 and the patient. A light source 13 is positioned at a location which is three meters from flat mirror 12 and a viewing means, which in a particular embodiment for use in a photographic operation is a camera 14, is positioned at the same location. In such an embodiment the light source is a flash unit and the camera can be any suitable and conventional 35 mm. camera such as a Canon AE-1 camera made by Canon Company of Lake Success, N.Y., having a 100 mm. lens.

Thus, the camera lens is 5 meters from the one diopter concave mirror and the flat mirror is simply used to fold the optical path, as shown. Since the concave mirror has a one diopter power, the pupil of the patient's eye in the embodiment depicted must be 1.25 meters from the concave mirror for it to be focused at the camera lens. If the patient's eye and the camera were both placed on the axis of the concave mirror, the patient's head would block its own reflection. To avoid such condition, the camera and eye are both positioned slightly off-axis. It has been found that a 7°-10° off axis alignment eliminates the physical interference of the patient's head and yet produces no optical distortion. The rays in FIG. 1 represent those coming from the eye of an emmetropic patient.

In using the technique of this invention as depicted in FIG. 1, four factors in the design of the system are primarily considered: the illumination of the fundus of the eye, the position and size of the pupil image, the position of the fundus image, and the size and quality of the fundus image.

For illumination, the light source can include, for example, a fiber optical bundle which is 3 mm. in diameter used to transport light from the camera's flash unit so as to emit the light from the flash unit on the optic axis of the camera lens. The light source is optically 5 meters from the concave mirror and is brought to a focus at the patient's cornea as depicted in FIG. 2. The image of the light source is minified by 0.25X in the particular embodiment depicted so that the corneal reflection is less than 1 mm. in diameter. The light then spreads to illuminate about 10° of the fundus.

The patient's pupil is in turn focused by the mirror at the camera lens. In the embodiment shown, it is magnified by 4X so that, at low ambient illumination levels, the pupil image is about 25 mm. in diameter. The fundus is imaged by the concave mirror as shown by the fundus image 15 in the figures. If the patient is emmetropic the concave mirror treats the fundus as an object at infinity and focuses it at one meter, which positions it at 4 meters from the camera, the distance at which the camera is normally focused. If the patient is myopic, the fundus image is closer to the camera, e.g., 2 meters for a +4D hyperope, 1.33 meters for a +8D hyperope, and 0.8 meter for a 16D hyperope. If the patient is hyperope the fundus image is further from the camera. The fundus of a −4D is focused by the eye at a distance of 0.25 meters from the cornea. Such position is one meter from the concave mirror and thus the camera must be focused at infinity. Greater degrees of myopia require that an auxiliary minus lens be placed on the camera lens. A minus one diopter auxiliary lens allows the system to photograph the fundus of patients with refractive errors up to −20D of myopia.

The area of the fundus that can be viewed depends on the diameter of the concave mirror and the distance of the patient from the concave mirror. With a mirror diameter of 20 cm. and a 125 cm. distance between the patient's eye and the mirror, approximately 9.3° of the fundus is the angle theoretically visible. The pupil image at the camera lens is so large that it is not a factor. The mirror used preferably should be ground to a precision in excess of that needed for fundus photography. Such a mirror has been found to produce no distortions or peripheral aberrations and, if the camera is properly focused, the image quality has been found to be excellent.

If the 35 mm. camera and flash unit are replaced by an ophthalmoscope, an examiner can readily view the fundus directly. For a cooperative patient this would normally be a relatively easy technique to perform but may have no clear-cut advantages over conventional direct ophthalmoscopy. The advantage in the technique of the invention lies with its use with the wary or uncooperative patient. In direct ophthalmoscopy, the constant high illumination produced by the ophthalmoscope will cause pupil constriction and the patient may tend to look at the light or to move aside to avoid the light. Lack of patient cooperation would permit the ophthalmoscopist to take only a series of brief looks at different fundus regions. If the examiner is willing to view the fundus in such brief glances, the examination can be readily accomplished because between viewings the patient is sitting comfortably in the dark with no object or person being close enough to his or her face to offer a threat of any nature. The patient is unlikely to get as upset as when other forms of ophthalmoscopy are used.

In some applications it is desirable that the field of view of the fundus be greater than 10° for use with a fundus camera. For example, it may be desirable that the fundus camera photograph a field as high as 20° or so. To increase the fundus area a larger concave mirror having a shorter focal length can be used. For example, a 25 cm. or 30 cm. concave mirror with a focal length of 0.5 meters would be acceptable. If the mirror is placed 62.5 cm. from the patient's eye, which maintains the 4X magnification between the patient's pupil and the camera lens, such mirrors would provide about a 23° and a 28° fundus angle, respectively.

Even large mirrors can be used, although such mirrors tend to become quite expensive for normal use. Mirrors with shorter focal lengths provide a larger fundus angle but many require that the instruments be placed further off the optical axis than the 7°-10° discussed above. Placement too far off might place undesired distortions and aberrations. It has been found that a 25 cm. mirror described above requires an alignment of the eye and camera at about 9° off-axis, while a 30 cm. mirror requires more than a 10° off-axis alignment. Generally then concave mirrors having a diameter in a range between about 20 cm. to about 40 cm. and a focal length in a range from about ⅓ to 1 meter will be acceptable for substantially all applications in which the invention is used.

As to the selection of a concave mirror, quality concave mirrors with diameters great than 25 cm. are available for use in telescopes. In order to focus an object at infinity, a concave paraboloidal mirror surface is normally needed. However, for a narrow field (i.e. a field of less than 10°) a spherical mirror having virtually the same curve as a paraboloid can be used. For larger fields a spherical mirror has a positive spherical aberration. If, on the other hand, one wished to focus an object back on itself, or near itself, a spherical mirror tends to be ideal for a large field, while a paraboloidal mirror might have serious negative spherical aberrations.

The in-between condition of focusing an object at one point to an image at another point ideally requires an ellipsoidal mirror within focus at the object and the other at the image. With a requirement of the invention that the camera be 4 times as far from the mirror as the patient's eye, an ellipsoidal mirror should have a major axis length which is 1.25 times that of its minor axis. Such an ellipsoidal mirror is not readily obtainable. However, the shape of a spherical mirror for a 45° field is virtually identical to such an ellipsoidal mirror, and so, a spherical mirror, rather than a parabolic telescope mirror, can be used. Spherical mirrors are more easily manufactured and less expensive than telescope mirrors and would be useful in the invention.

Telescope mirrors are normally ground to an overall surface accuracy of a fraction of a wavelength. For example, a 25 cm. mirror that has been used in the invention has surface accuracy of 0.125 wavelength or better. Such accuracy is essential for a light collector which is used without an aperture. However, the fundus is projected through an aperture, i.e., the pupil of the eye. If the patient's eye is emmetropic, the light rays from any point on the fundus would emerge in parallel and be reflected by a region of the mirror that is the same size as the patient's pupil. If the patient is ametropic the light from any point on the fundus will diverge or converge and, thus, strike a larger region of the mirror. A seven diopter refractive error spreads the light from a fundus point to a 5 cm. circle at the concave mirror while an eleven diopter error spreads the beam to 7.5 cm. at the concave mirror. If a slightly reduced image quality is accepted for patients with high refractive errors, the optical quality requirements of the mirror are significantly reduced.

Additional considerations that must be taken into account when using the technique of the invention are the same as those for other fundus camera systems: Such considerations include patient position and stability, focusing the triggering of the camera, and the fundus region to be photographed. When the patient is positioned at between a half to a full meter from the mirror, the patient clearly feels that his or her face is not threatened by the presence of a nearby instrument. However, the patient's pupil must still be at approximately the correct position for viewing the fundus. For a moderately cooperative patient a conventional chin cup arrangement provides good stability. For infants, the use of a set of distant pointers would allow the infant's eye to be placed in approximately the correct position. If the infant is sitting back in a dark room, its eye is usually stable enough for photography and precise alignment then requires that the camera be moved into precise position.

Non-mydriatic fundus cameras generally use infrared television monitoring of the fundus and each monitoring would also facilitate the use of the system of the invention. In one embodiment of the technique of the invention a red LED (light emitting diode) was attached to the camera viewfinder and the light therefrom was projected by the camera lens and focused by the concave mirror at the patient's pupil. In this way, the photographer was able to trigger the camera when the red spot from the LED was relatively small (focused) and centered on the cornea. Such technique made it relatively easy to assure proper positioning within the focal plane and accomodation was not a problem.

When using the technique of the invention it is relatively easy to obtain patient cooperation for photographing different parts of the fundus. Since the patient is in open space, an illuminated fixation target can be moved to any position relative to the mirror. For example, in a dark room infants can fixate on an illuminated toy 16, as shown in FIG. 1, thereby allowing the examiner to carefully control the fundus position being photographed.

What is claimed is:

1. A system for performing an examination of the eye of a subject comprising
   a source of light
   a concave mirror, having a focal length in a range from about $\frac{1}{2}$ to about 1 meter for receiving the light from said source and focusing said light at a selected region of the fundus of the eye of said subject, an enlarged optical image of said selected region of the eye thereby being formed at a selected spatial region remote from said eye; and
   viewing means capable of being focused at said selected spatial region for permitting said image to be viewed for examination of said selected region of the eye.

2. A system in accordance with claim 1 wherein said viewing means is an ophthalmoscope for permitting immediate viewing of the enlarged optical image of said selected region of an eye of said subject.

3. A system in accordance with claim 1 wherein said viewing means is a camera, the image of said selected region of the eye of said subject being photographed for subsequent viewing thereof; and
   said source of light is a light flash unit operable in combination with said camera during the photographing of said image.

4. A system in accordance with claim 1 wherein said concave mirror is positioned at a distance which is greater than one and up to two times said focal length from the eye of said subject.

5. A system in accordance with claim 1 wherein said concave mirror has a diameter within a range from about 20 cm. to about 40 cm.

6. A system in accordance with claim 1 and further including at least one flat mirror positioned in the optical path between said concave mirror and said viewing means intermediate said concave mirror and said viewing means to provide a folded optical path therebetween.

7. A system in accordance with claim 6 wherein said at least one flat mirror is positioned in said optical path at a location which is remote from and not in the field of view of said subject.

* * * * *